(12) United States Patent
Injev

(10) Patent No.: US 7,758,546 B2
(45) Date of Patent: Jul. 20, 2010

(54) VARIABLE FLOW DEVICE

(75) Inventor: Valentine P. Injev, Irvine, CA (US)

(73) Assignee: Alcon, Inc., Hunenburg (CH)

( * ) Notice: Subject to any disclaimer, the term of this patent is extended or adjusted under 35 U.S.C. 154(b) by 655 days.

(21) Appl. No.: 11/046,449

(22) Filed: Jan. 28, 2005

(65) Prior Publication Data

US 2006/0173403 A1    Aug. 3, 2006

(51) Int. Cl.
*A61M 1/00* (2006.01)
(52) U.S. Cl. .......................... 604/119; 604/35
(58) Field of Classification Search ............ 604/30–35, 604/118–121, 264, 65, 67; 606/107
See application file for complete search history.

(56) References Cited

U.S. PATENT DOCUMENTS

| | | | |
|---|---|---|---|
| 3,882,872 A * | 5/1975 | Douvas et al. .............. 606/107 |
| 5,106,367 A | 4/1992 | Ureche et al. | |
| 5,167,620 A | 12/1992 | Ureche et al. | |
| 5,429,601 A * | 7/1995 | Conley et al. ................ 604/65 |
| 5,476,448 A | 12/1995 | Urich | |
| 5,515,930 A * | 5/1996 | Glaser ......................... 173/115 |
| 5,712,543 A * | 1/1998 | Sjostrom ....................... 318/71 |
| 5,782,634 A * | 7/1998 | Lingenhole et al. ......... 433/132 |
| 5,827,218 A * | 10/1998 | Nguyen et al. ................ 604/30 |
| 6,719,011 B2 | 4/2004 | Cull et al. | |
| 6,752,795 B2 | 6/2004 | Cull | |
| 2004/0077993 A1* | 4/2004 | Cionni ......................... 604/31 |
| 2005/0054971 A1* | 3/2005 | Steen et al. .................... 604/22 |

* cited by examiner

Primary Examiner—Matthew F Desanto

(57) ABSTRACT

A surgical handpiece having an active flow restrictor responsive to a feedback loop that can vary the fluid flow resistance through the handpiece.

15 Claims, 4 Drawing Sheets

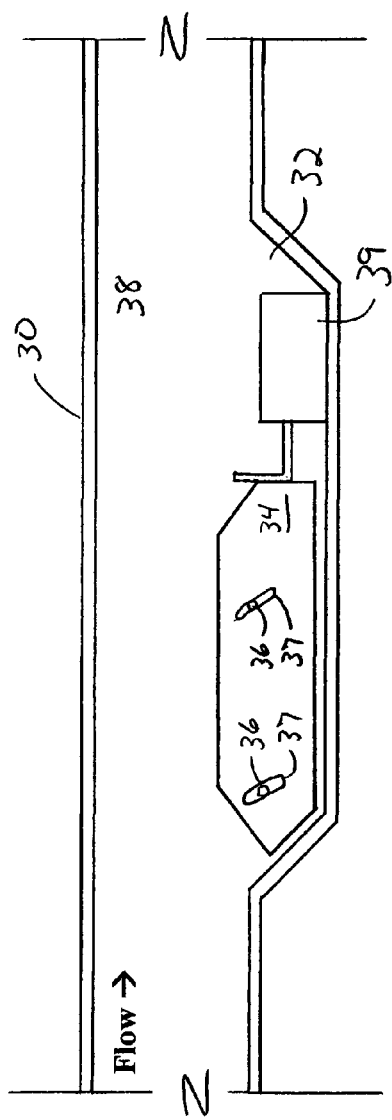
FIG. 2
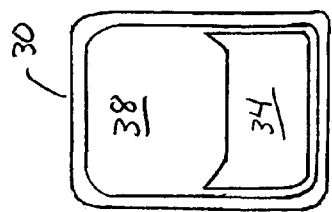
FIG. 4
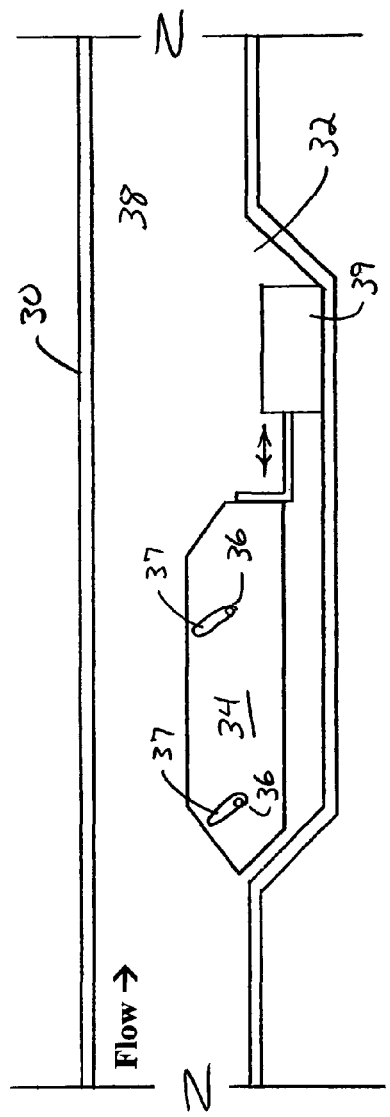
FIG. 3
FIG. 5

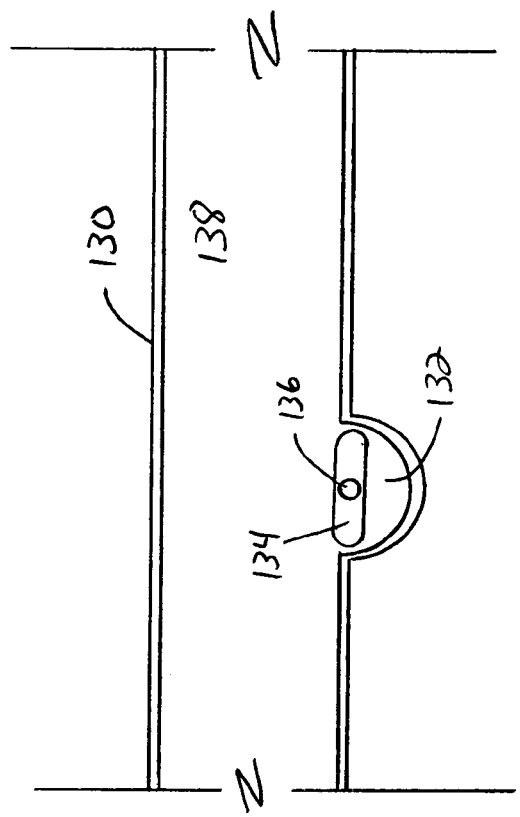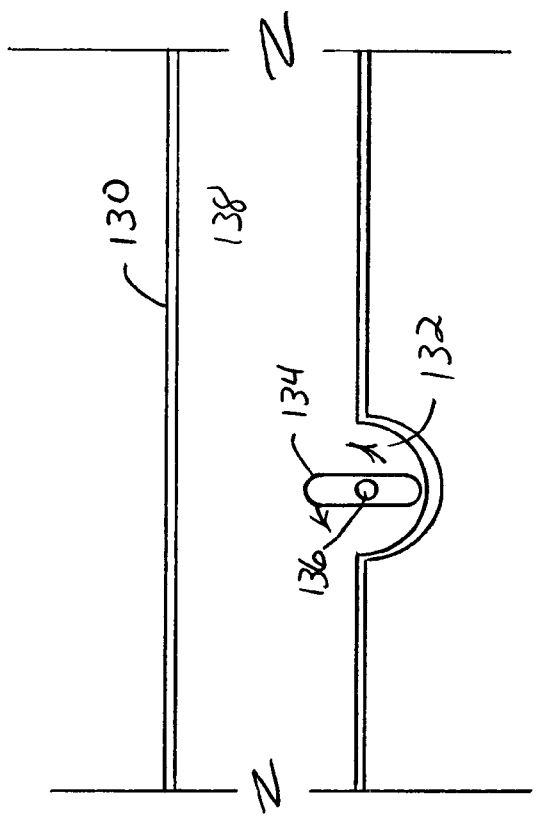

VARIABLE FLOW DEVICE

BACKGROUND OF THE INVENTION

This invention relates generally to the field of eye surgery and more particularly to the field of cataract surgery.

Phacoemulsification is a well-known process that refers to the use of a phacoemulsification machine that generates ultrasonic sound waves at the tip of a handpiece phacoemulsification machines are particularly useful in cataract surgery, for example, where it is necessary to remove a cataract lens from an eye. The tip is placed into the eye and specifically against the lens or cataract of the eye where the ultrasonic energy emulsifies the lens. The tip is hollow and emulsified pieces of the cataract are aspirated into an aspiration port formed at an end of the tip for removal from the eye. The aspirated cataract material flows through the tip, through channels within the handpiece and into an aspiration line connected to the phacoemulsification machine while fluid flows into the eye through an infusion line and an infusion sleeve formed around the tip to maintain the eye's pressure and shape.

Aspiration is driven by pumps housed within the phacoemulsification machine and infusion is typically generated by gravity. The fluid infused into the eye through the infusion sleeve also serves to suspend particles of lenticular debris within the infused fluid and the suspension is then aspirated through the aspiration line back to the phacoemulsification machine where it is collected in a receptacle. The flow created in the aspiration line generates a vacuum or negative pressure in the aspiration line and at the handpiece tip. The vacuum holds the lens material against the aspiration port of the tip where the material is emulsified.

The stronger the vacuum force is that holds the material against the aspiration port, i.e., "holdability", the more efficient emulsification becomes. Additionally, increasing holdability allows the surgeon to manipulate lens material within the handpiece tip more easily. Holdability increases with vacuum level and aspiration port size. Therefore, higher vacuum levels and larger aspiration ports lead to more efficient phacoemulsification. However, these parameters also risk sudden collapse of the anterior chamber of the eye as fluid rapidly rushes into the aspiration port due to the large aspiration port area and the high vacuum.

For example, during aspiration of the lenticular debris, the handpiece tip often becomes occluded with this debris. When it does, the vacuum level within the aspiration line builds to a high level. Eventually, the ultrasonic sound waves at the tip emulsify the debris, freeing the occlusion at the tip and resulting in an "occlusion break". Fluid then rapidly rushes into the aspiration port and aspiration line to satisfy the high vacuum built up in the tip and the aspiration line. This can create negative pressure in the anterior chamber relative to the posterior segment of the eye. When this occurs, the anterior chamber can collapse or the posterior capsule can shift anteriorly, both being undesirable during intraocular surgery, perhaps resulting in complications such as posterior capsule rupture.

To reduce the potential surge inflow of fluid in the aspiration line resulting from an occlusion break at the tip, emulsification tips have been manufactured in the past with a narrow lumen within the shaft of the tip that allows the surgeon to increase vacuum levels while limiting the sudden inflow of fluid in the aspiration line following an occlusion break. However, in these tip designs, the narrow portion of the lumen often becomes occluded with debris resulting in a complete loss of negative pressure or holdability at the aspiration port of the tip. The occlusion can be broken by refluxing fluid, prolonged application of ultrasonic energy or sometimes by increasing the vacuum level in the aspiration line. However, these techniques either increase the risk of complications, such as thermal injury to ocular tissues, or decrease efficiency of the emulsification surgical procedure. Additionally, these tip designs tend to have thinner walls than standard tips and are relatively fragile and more prone to breakage.

Thus, there is a need for a phacoemulsification system and/or handpiece that reduces the danger of sudden post occlusion surge inflow of fluid within the aspiration line following an occlusion break. There is still also a need for a phacoemulsification system that minimizes the risk of injury to the human eye during a phacoemulsification surgical procedure.

BRIEF SUMMARY OF THE INVENTION

The present invention addresses the deficiencies in the prior art by providing a surgical handpiece having an active flow restrictor responsive to a feedback loop that can vary the fluid flow resistance through the handpiece.

Accordingly, one objective of the present invention is to provide a surgical handpiece having an active flow restrictor.

Another objective of the present invention is to provide a surgical handpiece that reduces the danger of sudden post occlusion surge inflow of fluid within the aspiration line following an occlusion break.

Another objective of the present invention is to provide a phacoemulsification system that minimizes the risk of injury to the human eye during a phacoemulsification surgical procedure.

These and other advantages and objectives of the present invention will become apparent from the detailed description and claims that follow.

BRIEF DESCRIPTION OF THE DRAWINGS

FIG. 2 is a partial longitudinal cross-section of a first embodiment of the handpiece of the present invention illustrating the active flow restrictor in a first, less restricted position.

FIG. 3 is a partial longitudinal cross-section of a first embodiment of the handpiece of the present invention illustrating the active flow restrictor in a second, more restricted position.

FIG. 4 is a transverse cross-section of a first embodiment of the handpiece of the present invention taken at line 4-4 in FIG. 2.

FIG. 5 is a transverse cross-section of a first embodiment of the handpiece of the present invention taken at line 5-5 in FIG. 3.

FIG. 8 is a partial longitudinal cross-section of a third embodiment of the handpiece of the present invention illustrating the active flow restrictor in a first, less restricted position.

FIG. 9 is a partial longitudinal cross-section of a third embodiment of the handpiece of the present invention illustrating the active flow restrictor in a second, more restricted position.

DETAILED DESCRIPTION OF THE INVENTION

Figure 1:
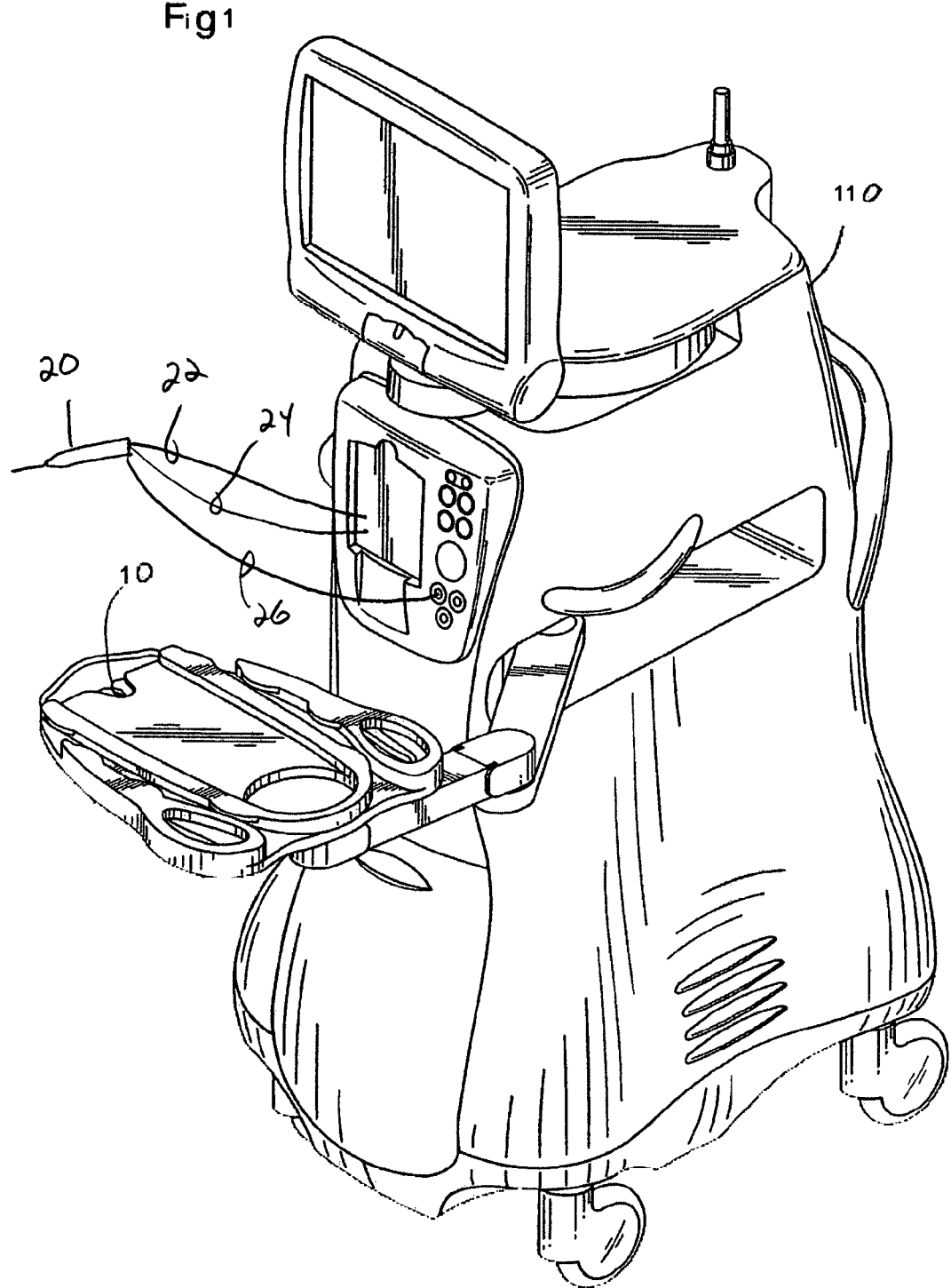
FIG. 1 is a perspective view of a surgical system that may be used with the present invention.

As best seen in FIG. 1, commercially available surgical systems generally include surgical console 110 having attached, adjustable mayo tray 10 and handpiece 20 attached to console 110 by aspiration tubing 22, irrigation tubing 24 and power cable 26. Power to handpiece 20 as well as the flows of irrigation and aspiration fluid is controlled by console 110, which contains appropriate hardware and software, such as power supplies, pumps, pressure sensors, valves, all of which are well-known in the art.

As best seen in FIGS. 2 and 3, handpiece 30 of the present invention may be of construction similar to that of conventional handpiece 20, except handpiece 30 contains enlarged portion 32 and movable restrictor 34 that is moved within enlarged portion 32 by linear actuator 39, pins 36 and slots 37. As best seen in FIGS. 4 and 5, the shape of restrictor 34 and main flow channel 38 within handpiece 30 is such that regardless of the position of restrictor 34, flow channel 38 remains rounded or oval. This is because a round or rounded geometry provides maximum flow per unit area with the least amount or parasitic fluidic losses.

As best seen in FIG. 2, is a relaxed, or least restricted state, restrictor 34 is located near the bottom or enlarged portion 32 so that flow channel 38 has its widest cross-section area, thereby providing the least resistance to fluid flow. As best seen in FIG. 3, under circumstances directed by the user or pre-programmed into the software in console 110, restrictor 34 can be elevated up into flow channel 38 by being moved linearly in both directions by linear actuator 39, forcing slots 37 to ride up or down pins 36, thereby restricting the cross-sectional area of flow channel 38, as seen in FIG. 5, and increase the flow resistance in flow channel 38. The movement of linear actuator 39 and the respective movement of restrictor 34 can be controlled in either direction via a feedback loop tied to pressure (vacuum) in flow channel 38 in an automated, pre-programmed manner, or to some other parameter under the control of the user of console 110.

Figure 6:
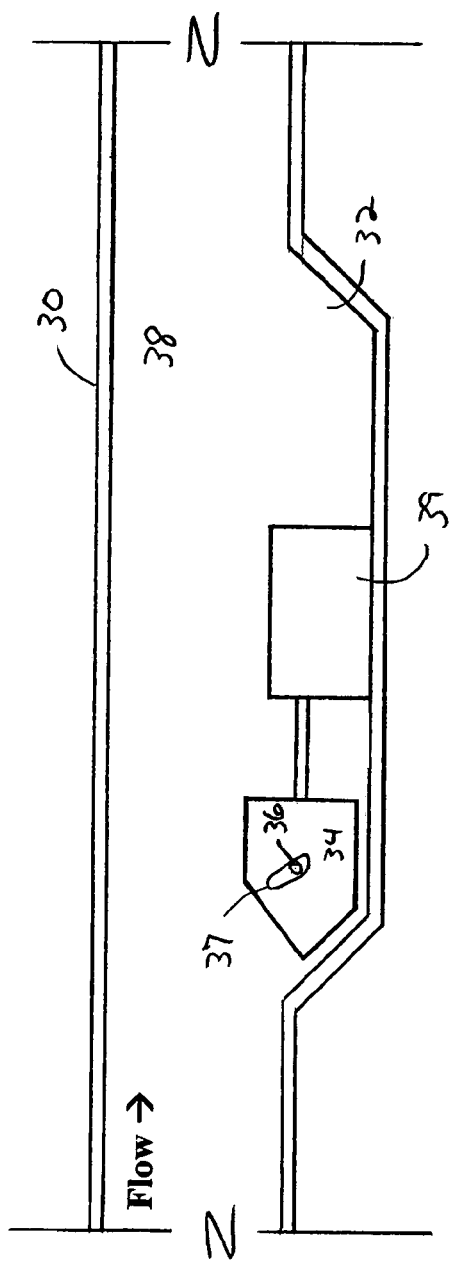
FIG. 6 is a partial longitudinal cross-section of a second embodiment of the handpiece of the present invention illustrating the active flow restrictor in a first, less restricted position.
Figure 7:
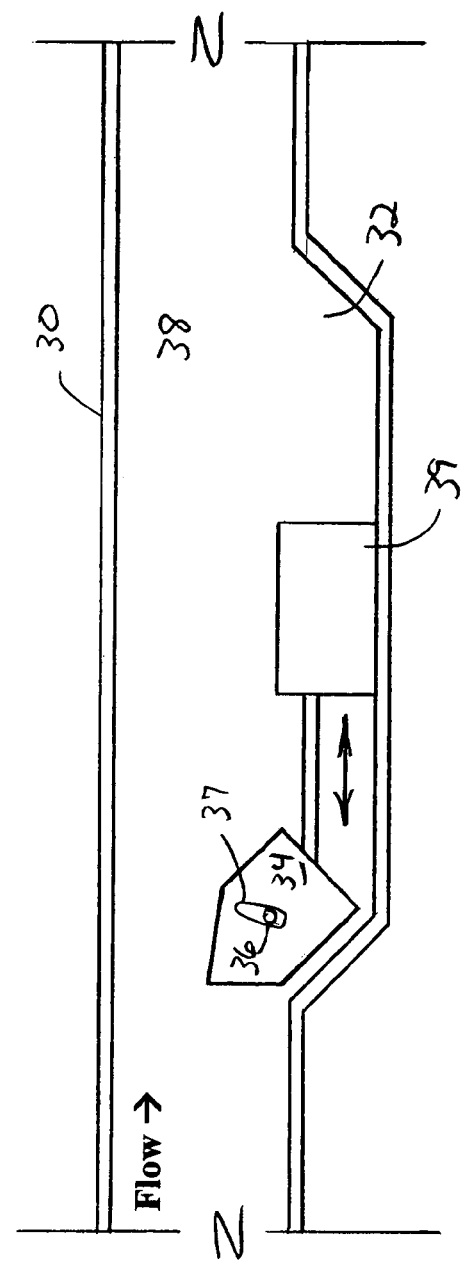
FIG. 7 is a partial longitudinal cross-section of a second embodiment of the handpiece of the present invention illustrating the active flow restrictor in a second, more restricted position.

Alternatively, as seen in FIGS. 6 and 7, linear movement of restrictor 34 by linear actuator 39 causes restrictor 34 it rotate eccentrically about pin 36, thereby restricting the cross-sectional area of flow channel 38.

As best seen in FIGS. 8 and 9, in a second embodiment of the present invention, handpiece 130 may contain flow channel 138 having enlarged portion 132 and flow restrictor 134 more in the shape of a paddle that rotates on shaft 136. Rotation of shaft 136 cause rotation of restrictor 134 from a first, position introducing little or no flow restriction in flow channel 138, as seen in FIG. 6, to a position that introduces a varying amount of restriction within flow channel 138, as seen in FIG. 8. The rotation of shaft 136 and the respective movement of restrictor 134 can be controlled via a feedback loop tied to pressure (vacuum) in flow channel 138 in an automated, pre-programmed manner, or to some other parameter under the control of the user of console 110.

This description is given for purposes of illustration and explanation. It will be apparent to those skilled in the relevant art that changes and modifications may be made to the invention described above without departing from its scope or spirit. For example, it will be recognized by those skilled in the art that the restrictor of the present invention may be placed anywhere along the aspiration fluid pathway, such as in the cassette formed as part of the console.

I claim:

1. A surgical system, comprising:
    a surgical console;
    a handpiece, the handpiece coupled to the surgical console by an irrigation tubing and an aspiration tubing;
    an aspiration fluid channel, with an enlarged portion located within the handpiece, coupled to the aspiration tubing; and
    a movable flow restrictor in the enlarged portion of the aspiration fluid channel, the movable flow restrictor moving in response to a command provided by the surgical console to vary fluid flow resistance in the aspiration fluid channel in response to a sensed vacuum pressure in the aspiration fluid channel;
    wherein the command provided by the surgical console to vary fluid flow resistance in the aspiration fluid channel is provided to the handpiece through a control cable connecting the handpiece to the surgical console;
    wherein the movable flow restrictor is coupled to a linear actuator and wherein linear movement of the linear actuator moves the movable flow restrictor to increase or decrease a cross sectional area of the aspiration fluid channel available for fluid flow;
    wherein the linear actuator is configured to move the movable flow restrictor in an automated, pre-programmed manner to increase or decrease a cross sectional area of the aspiration fluid channel available for fluid flow in response to the command provided by the surgical console;
    wherein the command is provided via a feedback loop with input associated with pressure sensed in the aspiration fluid channel.

2. The system of claim 1,
    wherein the aspiration fluid channel comprises a main flow channel having a first cross sectional area for fluid flow and wherein a portion of the main flow channel additionally comprises the enlarged portion having a second cross sectional area; and
    wherein, at the enlarged portion, the aspiration fluid channel has a cross sectional area comprising the first cross sectional area and the second cross sectional area.

3. The system of claim 2, wherein the movable flow restrictor moving in response to the command comprises the movable flow restrictor moving at least partially into the first cross sectional area of the main flow channel to reduce an area available for fluid flow in the aspiration fluid channel.

4. The system of claim 3, wherein the first cross sectional area comprises a round or oval geometry and wherein the area available for fluid flow in the aspiration fluid channel after movement of the movable flow restrictor at least partially into the main flow channel maintains a round or oval geometry.

5. The system of claim 1 wherein the flow restrictor has at least one slot along which the restrictor moves.

6. The system of claim 1, wherein the movable flow restrictor comprises at least one slot and wherein movement of the movable flow restrictor is at least partially guided by engagement of the at least one slot with at least one corresponding pin.

7. A surgical system, comprising:
    a surgical console;
    a handpiece communicably coupled to the surgical console;
    a flow channel, wherein aspiration fluid flow from the handpiece is at least partially aspirated through the flow channel; and a movable flow restrictor configured to move in the flow channel to increase or decrease a cross sectional area for fluid flow in the flow channel, wherein the movable flow restrictor is configured to move in the flow channel in response to a command from the surgical console to vary flow resistance in the flow channel;

wherein the movable flow restrictor is configured to be moved to increase or decrease a cross sectional area of the flow channel available for fluid flow;

wherein the movable flow restrictor is configured to be moved in an automated, pre-programmed manner to increase or decrease a cross sectional area of the flow channel available for fluid flow in response to the command provided by the surgical console;

wherein the command is provided via a feedback loop with input associated with pressure sensed in the flow channel.

8. The surgical system of claim 7, wherein an actuator is configured to move the movable flow restrictor when the actuator receives the command from the surgical console to vary flow resistance in the flow channel.

9. The system of claim 7,
wherein the flow channel comprises a first cross sectional area for fluid flow and wherein a portion of the flow channel additionally comprises an enlarged portion having a second cross sectional area;

wherein, at the enlarged portion, the flow channel has a cross sectional area comprising the first cross sectional area and the second cross sectional area; and wherein the movable flow restrictor moving in response to the command comprises the movable flow restrictor moving at least partially into the first cross sectional area of the flow channel to reduce an area available for fluid flow in the flow channel.

10. The system of claim 7, wherein the movable flow restrictor comprises at least one slot and wherein movement of the movable flow restrictor is at least partially guided by engagement of the at least one slot with at least one corresponding pin.

11. The system of claim 7, wherein the movable flow restrictor comprises a paddle that rotates to vary fluid flow resistance in the flow channel when the movable flow restrictor receives the command provided by the surgical console.

12. The system of claim 7, wherein the movable flow restrictor comprises a paddle that rotates to vary fluid flow resistance in the aspiration fluid channel when the movable flow restrictor receives a command provided by the surgical console.

13. A surgical handpiece, comprising:
a flow channel configured to aspirate fluid from the handpiece; and
a movable flow restrictor configured to move in the flow channel in the handpiece to increase or decrease a cross sectional area for fluid flow in the flow channel, wherein the movable flow restrictor is configured to move in the flow channel in response to receiving a command from a surgical console to vary flow resistance in the flow channel;

wherein the movable flow restrictor is movable to increase or decrease the cross sectional area of the flow channel available for fluid flow;

wherein the movable flow restrictor is configured to move in an automated, pre-programmed manner to increase or decrease the cross sectional area of the flow channel available for fluid flow in response to the command provided by the surgical console;

wherein the command is provided via a feedback loop with input associated with pressure sensed in the flow channel.

14. The surgical handpiece of claim 13,
wherein the flow channel comprises a first cross sectional area for fluid flow and wherein a portion of the flow channel additionally comprises an enlarged portion having a second cross sectional area;

wherein, at the enlarged portion, the flow channel has a cross sectional area comprising the first cross sectional area and the second cross sectional area; and wherein the movable flow restrictor moving in response to receiving the command comprises the movable flow restrictor moving at least partially into the first cross sectional area of the flow channel to reduce an area available for fluid flow in the flow channel.

15. The system of claim 13, wherein the movable flow restrictor comprises a paddle that rotates to vary fluid flow resistance in the aspiration fluid channel when the movable flow restrictor receives a command provided by the surgical console.

* * * * *